(12) United States Patent
Lee et al.

(10) Patent No.: US 9,801,794 B2
(45) Date of Patent: Oct. 31, 2017

(54) INORGANIC POWDER COATED WITH BIOCOMPATIBLE POLYMER, AND COSMETIC COMPOSITION COMPRISING SAME

(71) Applicant: AMOREPACIFIC CORPORATION, Seoul (KR)

(72) Inventors: Hyun Suk Lee, Yongin-si (KR); Jun Oh Kim, Yongin-si (KR); Young Jun Yang, Yongin-si (KR); Song Seok Shin, Yongin-si (KR); Kyung Ho Choi, Yongin-si (KR); Yeong Jin Choi, Yongin-si (KR); Young Ho Park, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 0 days.

(21) Appl. No.: 14/431,663

(22) PCT Filed: Nov. 29, 2013

(86) PCT No.: PCT/KR2013/010996
§ 371 (c)(1),
(2) Date: Mar. 26, 2015

(87) PCT Pub. No.: WO2014/084657
PCT Pub. Date: Jun. 5, 2014

(65) Prior Publication Data
US 2015/0272838 A1    Oct. 1, 2015

(30) Foreign Application Priority Data

Nov. 30, 2012 (KR) .......... 10-2012-0137787

(51) Int. Cl.
| | |
|---|---|
| *A61K 8/02* | (2006.01) |
| *A61K 49/04* | (2006.01) |
| *B82Y 5/00* | (2011.01) |
| *A61Q 19/00* | (2006.01) |
| *A61K 8/29* | (2006.01) |
| *A61K 8/81* | (2006.01) |
| *A61Q 1/12* | (2006.01) |
| *A61K 8/26* | (2006.01) |
| *A61Q 17/04* | (2006.01) |

(52) U.S. Cl.
CPC .......... *A61K 8/0241* (2013.01); *A61K 8/26* (2013.01); *A61K 8/29* (2013.01); *A61K 8/8152* (2013.01); *A61K 49/0423* (2013.01); *A61Q 1/12* (2013.01); *A61Q 17/04* (2013.01); *A61Q 19/00* (2013.01); *B82Y 5/00* (2013.01); *A61K 2800/624* (2013.01); *A61K 2800/651* (2013.01)

(58) Field of Classification Search
CPC .......... A61K 8/0241; A61K 49/0423; A61K 2800/624; A61K 2800/651; A61K 8/29; A61K 8/8152; A61K 8/26; B82Y 5/00; A61Q 19/00; A61Q 1/12; A61Q 17/04
See application file for complete search history.

(56) References Cited

U.S. PATENT DOCUMENTS

| | | | | |
|---|---|---|---|---|
| 2003/0118530 | A1* | 6/2003 | O'Brien .......... | A61K 8/02 424/63 |
| 2012/0082708 | A1* | 4/2012 | Lee .......... | A61K 8/19 424/401 |
| 2014/0288259 | A1* | 9/2014 | Yu .......... | A61Q 17/04 528/19 |

FOREIGN PATENT DOCUMENTS

| | | | | |
|---|---|---|---|---|
| CN | 101157745 | A | 4/2008 | |
| JP | 2005194212 | | 7/2005 | |
| JP | 2008-137944 | * | 6/2006 | .......... A61K 8/25 |
| JP | 2008137944 | | 6/2008 | |
| JP | 2008143836 | | 6/2008 | |
| KR | 1020110062501 | | 6/2011 | |
| KR | 1020120034919 | | 4/2012 | |
| KR | 1020120034920 | | 4/2012 | |
| KR | WO2013/081217 | * | 6/2013 | .......... A61K 8/89 |

OTHER PUBLICATIONS

JP2008-137944 Translation.*
"Lipidure-HM, PMB" product information (downloaded Oct. 18, 2016 from http://www.nofamerica.com/store/index.php?dispatch=categories.view&category_id=152).*
Taketoshi Minato, et al, The Electronic Structure of Oxygen Atom vacancy and Hydroxyl Impurity Defects on Titanium Dioxide (110) Surface. 130 J Chem. Phys. 124520 (2009).*
Ruriko Yokoyama et al., "Preparation and properties of biocompatible polymer-grafted silica nanoparticle", European Polymer Journal, vol. 42, p. 3221-3229, 2006.

* cited by examiner

*Primary Examiner* — Sean Basquill
(74) *Attorney, Agent, or Firm* — Cantor Colburn LLP

(57) ABSTRACT

The present invention relates to inorganic powder coated with biocompatible polymer and a cosmetic composition comprising same. More particularly, the present invention relates to an organic/inorganic composite powder in which the rough surface of the inorganic powder is treated with biocompatible polymer, thereby improving dispersibility and feeling of use and to a cosmetic composition comprising said composite powder so as to achieve improved feeling of use and tight adhesion when applied to the skin.

10 Claims, 1 Drawing Sheet

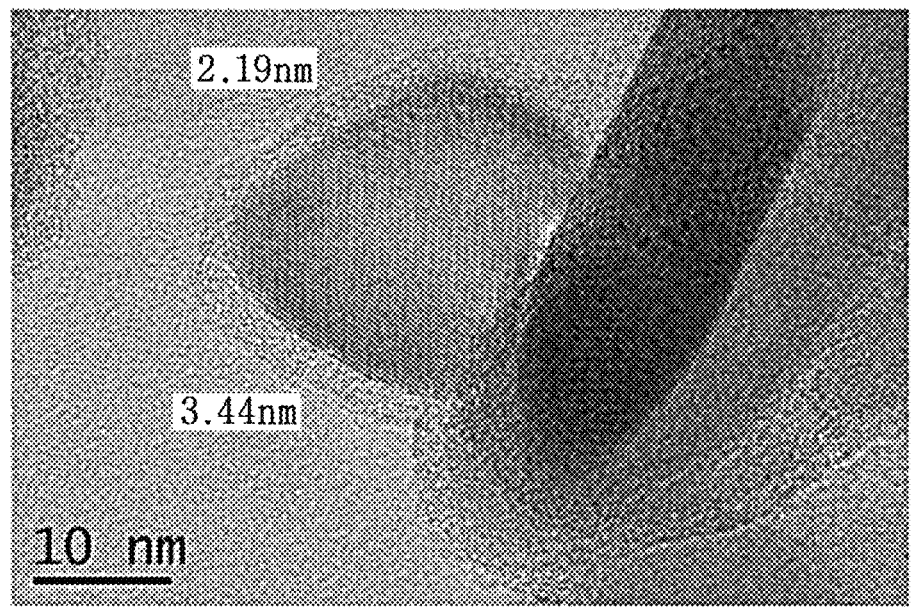

INORGANIC POWDER COATED WITH BIOCOMPATIBLE POLYMER, AND COSMETIC COMPOSITION COMPRISING SAME

TECHNICAL FIELD

The present disclosure relates to a novel organic-inorganic hybrid powder having improved dispersibility and usability and a cosmetic composition comprising the hybrid powder and exhibiting improved usability and adhesion when applied onto skin.

DESCRIPTION ABOUT NATIONAL RESEARCH AND DEVELOPMENT SUPPORT

This study was supported by the Korean Healthcare R&D Project of Ministry of Health & Welfare, Republic of Korea (Global Cosmetic R&D Management team, Project No. A103017) under the superintendence of Foundation of Korea Cosmetic Industry Institute.

BACKGROUND ART

The primary purpose of the commonly used cosmetics for makeup is to cover skin defects, provide transparency and brightness to the skin, protect the skin from ultraviolet (UV) rays, control sweat and sebum, or the like, thereby cleansing and protecting the skin and providing satisfaction. Various inorganic powders such as titanium dioxide, sericite, etc. are used in the cosmetic compositions for makeup for as UV block agent and pigment. However, these inorganic powders are disadvantageous in that they exhibit poor usability because of crystallinity or rough surface and dispersibility is remarkably reduced because of inter-particle aggregation. Accordingly, there have been many attempts of surface treatment of inorganic powder for use in cosmetic compositions to improve dispersibility and rough usability of the inorganic powder.

Until recently, skin-friendly materials have been physically adsorbed on the surface of inorganic powders for the purpose of such surface treatment. However, there are not many skin-friendly materials available and the weak physical treatment often leads to non-uniform surface treatment.

Accordingly, methods of chemically treating the surface of inorganic powders are attempted recently. For example, a method of directly grafting the biocompatible lipid-polymer 2-methacryloyloxyethylphosphorylcholine (MPC) on the surface of silica using a coupling agent having an isocyanate functional group (*European Polymer Journal* 42 (2006) 3221-3229) and a method of coating MPC on the surface of titanium dioxide using trichloroacetyl chloride (Korean Patent Application No. 10-2012-0065929) were reported. However, these methods are disadvantageous in that they require use of a metal catalyst such as molybdenum, use of toxic solvents such as toluene is necessary and a process of removing salts produced during the reaction has to be added.

Therefore, an economical, ecofriendly and simple process for uniformly coating the surface of an inorganic powder is necessary.

REFERENCES OF THE RELATED ART

Korean Patent Publication No. 10-2012-0034919
*European Polymer Journal* 42 (2006) 3221-3229

DISCLOSURE

Technical Problem

The present disclosure is directed to providing a novel organic-inorganic hybrid powder having a biocompatible polymer uniformly coated and thus having improved dispersibility and a cosmetic composition containing same.

Technical Solution

In a general aspect, there is provided an organic-inorganic hybrid powder wherein an inorganic powder is uniformly coated with a biocompatible polymer.

In another general aspect, there is provided a cosmetic composition comprising the organic-inorganic hybrid powder.

Advantageous Effects

An organic-inorganic hybrid powder according to the present disclosure may have improved dispersibility since the rough surface of an inorganic powder is coated with a biocompatible polymer.

A cosmetic composition containing the organic-inorganic hybrid powder may provide soft usability and superior adhesion.

DESCRIPTION OF DRAWINGS

FIG. 1 is a TEM image of titanium dioxide surface-treated with a biocompatible polymer according to an exemplary embodiment of the present disclosure.

BEST MODE

Hereinafter, the present disclosure is described in detail.

In an aspect, the present disclosure provides an organic-inorganic hybrid powder comprising an inorganic powder coated with a biocompatible polymer.

The inorganic powder used in the hybrid powder is not particularly limited, but an inorganic powder having a hydroxy functional group may be used. For example, one or more selected from titanium dioxide and sericite having a hydroxy functional group may be used.

And, the biocompatible polymer used to coat the surface of the inorganic powder may be one or more selected from 2-methacryloyloxyethylphosphorylcholine and 2-methacryloyloxyethylphospatidylcholine, although not being limited thereto.

In an exemplary embodiment of the present disclosure, the biocompatible polymer used to surface-treat the inorganic powder may be used in an amount of 0.1-8 wt % based on the total weight of the inorganic powder. If the content of the biocompatible polymer is less than 0.1 wt %, improvement of the dispersibility of the inorganic powder may be insufficient. And, if the content exceeds 8 wt %, it may lead to a negative effect such as aggregation of the inorganic powders.

In another aspect, the present disclosure provides a method for preparing the organic-inorganic hybrid powder, including:

1) reacting the surface of an inorganic powder having a hydroxy functional group with a coupling agent;

2) preparing an organic-inorganic hybrid powder by coating the inorganic powder of 1) with a biocompatible polymer; and 3) filtering and pulverizing the organic-inorganic hybrid powder of 2).

The coupling agent in 1) may be a coupling agent having a trimethoxysilyl group. For example, 3-(trimethoxysilyl) propyl methacrylate, 3-(trimethoxysilyl)propyl acrylate, etc. may be used, although not being limited thereto. And, the coupling agent may be used in an amount of 0.1-10 wt % based on the weight of the inorganic powder.

In 2), the biocompatible polymer may be uniformly coated on the surface of the inorganic powder by grafting.

And, the organic-inorganic hybrid powder may be prepared by reacting with the coupling agent at room temperature for 12 hours in 1) and coating the inorganic powder with the biocompatible polymer at 65-75° C. for 6-12 hours in 2).

The organic-inorganic hybrid powder prepared by the method according to the present disclosure has the biocompatible polymer uniformly dispersed on the surface of the inorganic powder and, thus, can solve the problem of rough surface or crystallinity of the inorganic powder.

In another aspect, the present disclosure provides a cosmetic composition containing the organic-inorganic hybrid powder according to the present disclosure.

In an exemplary embodiment of the present disclosure, the composition contains the organic-inorganic hybrid powder in an amount of 0.1-30 wt % based on the total weight of the composition.

Since the organic-inorganic hybrid powder according to the present disclosure has superior dispersibility when applied on skin, no inter-particle aggregation occurs. Accordingly, the cosmetic composition containing the hybrid powder can be softly applied on skin and provides improved usability. Also, it can provide superior adhesion to skin.

The composition according to the present disclosure can be prepared into a suncare or makeup products, although not being particularly limited in formulation. For example, it can be prepared into sunblock lotion, sunblock cream, makeup base, liquid foundation, powder foundation, powder pact, face powder, compact powder, etc.

Further, those skilled in the art can select and add adequate ingredients to the cosmetic composition of each formulation considering the particular formulation or purpose of use.

Hereinafter, the present disclosure will be described in detail through examples, formulation examples and test examples. However, the following examples, formulation examples and test examples are for illustrative purposes only and it will be apparent to those of ordinary skill in the art that the scope of the present disclosure is not limited by them.

In addition, it will be apparent to those of ordinary skill in the art that various modifications and alterations can be made without departing from the scope of this disclosure as set forth in the appended claims.

[Preparation Example 1] Preparation of Inorganic Powder Coated with Biocompatible Polymer Organic-inorganic hybrid powders of Examples 1 and 2 were prepared by a two-step process as follows.

Step 1: Binding of Coupling Agent to Surface of Inorganic Powder

An inorganic powder to which a coupling agent (3-(trimethoxysilyl)propyl methacrylate) is bound was prepared with the composition described in Table 1.

TABLE 1

| No. | Ingredients | Contents |
|---|---|---|
| 1 | Titanium dioxide having hydroxy functional group | 100 g |
| 2 | 3-(Tri methoxysilyl)propyl methacrylate | 10 g |
| 3 | Ethanol | 950 mL |
| 4 | Distilled water | 50 mL |

<Procedure>

1) The ingredients 1-4 described in Table 1 are mixed and stirred sufficiently.

2) The mixture of 1) is purged with nitrogen for 30 minutes and reaction is carried out at room temperature for 12 hours under stirring.

3) Upon completion of reaction, the reaction product is centrifuged. After removing the supernatant, the product is washed with ethanol at least 3 times to remove unreacted material and then is dried in a vacuum oven at 50° C.

Step 2: Preparation of Organic-Inorganic Hybrid Powder

Organic-inorganic hybrid powders coated with biocompatible polymers of Examples 1 and 2 were prepared with the compositions described in Table 2.

TABLE 2

| No. | Ingredients | Example 1 | Example 2 |
|---|---|---|---|
| 1 | Product of step 1 | 100 g | 100 g |
| 2 | 2-Methacryloyloxyethylphosphorylcholine | 5 g | — |
| 3 | 2-Methacryloyloxyethylphospatidylcholine | — | 5 g |
| 4 | AIBN initiator | 0.05 g | 0.05 g |
| 5 | Ethanol | 1000 mL | 1000 mL |

<Procedure>

1) The ingredients 1-5 described in Table 2 are mixed and stirred sufficiently.

2) The mixture of 1) is purged with nitrogen for 30 minutes and reaction is carried out at 65° C. for 6-12 hours under stirring.

3) Upon completion of reaction, the reaction product is centrifuged. After removing the supernatant, the product is washed with ethanol at least 3 times to remove unreacted material and is dried in a vacuum oven at 50° C. and then pulverized.

FIG. 1 shows a transmission electron microscopic (TEM) image of titanium dioxide (inorganic powder) coated with the biocompatible polymer of Example 1 prepared through Step 2. From FIG. 1, it can be seen that a coating film of a uniform thickness was formed on the surface of the inorganic powder.

[Preparation Example 2] Preparation of Hybrid Powder of Comparative Example 1

Titanium dioxide surface-treated with triethoxycaprylsilane of Comparative Example 1 was prepared in the same manner as in Preparation Example 1, except that triethoxycaprylsilane was used instead of the phospholipid 2-methacryloyloxyethylphosphorylcholine or 2-methacryloyloxyethylphospatidylcholine for surface treatment of the inorganic powder in the two-step process of Preparation Example 1.

[Test Example 1] Measurement of SPF of Organic-Inorganic Hybrid Powder In Vitro

In general, inorganic powders exhibit better ability of effectively blocking UV as the particles are uniformly dispersed without aggregation. Accordingly, the improvement in the dispersibility of the coated inorganic powders can be determined by measuring UV absorbance. To determine the UV blocking ability of the coated inorganic powders of Examples 1-2, SPF was measured in vitro at 310 nm using the SCINCO UV-Vis spectrophotometer S-3100. For comparison, the hybrid powder prepared in Preparation Example 2 (Comparative Example 1) and an inorganic powder with no coupling agent bound (Comparative Example 2) were used. The test result is given in Table 3.

TABLE 3

UV absorbance test result

|  | UV absorbance (AU) |
| --- | --- |
| Example 1 | 0.71 ± 0.23% |
| Example 2 | 0.68 ± 0.11% |
| Comparative Example 1 | 0.51 ± 0.17% |
| Comparative Example 2 | 0.44 ± 0.11% |

As seen from Table 3, the organic-inorganic hybrid powders of Examples 1-2 according to the present disclosure exhibited significantly (about 1.5 times) higher UV absorbance as compared to Comparative Examples 1-2. Accordingly, it can be seen that the organic-inorganic hybrid powder according to the present disclosure exhibits very superior UV blocking ability, suggesting that the dispersibility of the particle is greatly improved.

[Preparation Example 3] Preparation of Formulation Examples 1-2 and Comparative Formulation Example 1

Cosmetic compositions in the form of W/O emulsion were prepared according to a commonly employed method with the compositions described in Table 4.

TABLE 4

(content: wt %)

|  | Ingredients | Formulation Example 1 | Formulation Example 2 | Comparative Formulation Example 1 |
| --- | --- | --- | --- | --- |
| Oily ingredients | Butylene glycol dicaprylate/dicaprate | 6 | 6 | 6 |
|  | Triisononanoin | 4 | 4 | 4 |
|  | Octyl methoxycinnamate | 5 | 5 | 5 |
|  | Cyclopentasiloxane/cyclohexasiloxane | 15 | 15 | 15 |
|  | Tridecyl trimellitate | 3 | 3 | 3 |
|  | Dimethicone/vinyl dimethicone crosspolymer/cyclopentasiloxane/cyclohexasilicone | 2 | 2 | 2 |
|  | Lauryl PEG-9 polydimethylsiloxyethyldimethicone | 7.5 | 7.5 | 7.5 |
|  | Disteardimonium hectorite | 1.1 | 1.1 | 1.1 |
|  | Paraoxybenzoic acid ester | Adequate | Adequate | Adequate |
|  | Purified water | To 100 | To 100 | To 100 |
| Aqueous ingredients | Butylene glycol | 5.0 | 5.0 | 5.0 |
|  | Disodium EDTA | Adequate | Adequate | Adequate |
|  | TEA | Adequate | Adequate | Adequate |
|  | Imidazolinyl urea | Adequate | Adequate | Adequate |
| Powder ingredients | Organic-inorganic hybrid powder of Example 1 | 5 | — | — |
|  | Organic-inorganic hybrid powder of Example 2 | — | 5 | — |

<Procedure>

1) The oily ingredients and the powder ingredients are uniformly mixed while heating at 70-75° C.

2) The aqueous ingredients are uniformly dissolved and mixed while heating at 70-75° C.

3) An emulsion is prepared by adding the mixture of 1) to the mixture of 2) under stirring while maintaining the temperature at 70-75° C.

[Preparation Example 4] Preparation of Formulation Examples 3-4 and Comparative Formulation Example 2

Cosmetic compositions in the form of face powder were prepared according to a commonly employed method with the compositions described in Table 5.

TABLE 5

(content: wt %)

| | Ingredients | Formulation Example 3 | Formulation Example 4 | Comparative Formulation Example 2 |
|---|---|---|---|---|
| Powder ingredients | Talc (dimethicone treated) | To 100 | To 100 | To 100 |
| | Mica (dimethicone treated) | 30 | 30 | 30 |
| | Sericite (dimethicone treated) | 25 | 25 | 25 |
| | Silica | 5 | 5 | 5 |
| | Organic-inorganic hybrid powder of Example 1 | 5 | — | — |
| | Organic-inorganic hybrid powder of Example 2 | — | 5 | — |
| Oily ingredients | Polyglyceryl-2 triisostearate | 4 | 4 | 4 |
| | Dimethicone | 5 | 5 | 5 |
| Preservative | Polyoxyethylene hydrogenated castor oil | 2 | 2 | 2 |
| | Paraoxybenzoic acid ester | Adequate | Adequate | Adequate |

<Procedure>

1) The powder ingredients are uniformly mixed for 30 minutes using a Henschel mixer.
2) The oily ingredients and the preservative are uniformly dissolved by heating to 80° C.
3) The mixture of 2) is added to the powder ingredients of 1) by spraying while mixing. After mixing for 20 minutes, the mixture is pulverized and then filtered.

[Test Example 2] Usability Test

Thirty women of 25-35 years were asked to use Formulation Examples 1-4 and Comparative Formulation Examples 1-2 for a month, twice a day. Then, they were asked to evaluate the usability of the cosmetic formulations based on a 5-point scale on adhesion, spreadability, continuity, prevention of skin dryness, etc. The result is given in Table 6.

TABLE 6

Usability test result

| | Adhesion | Spreadability | Softness | Continuity | Prevention of dryness | Particle aggregation |
|---|---|---|---|---|---|---|
| Formulation Example 1 | 5 | 4 | 5 | 5 | 4 | 4 |
| Formulation Example 2 | 4 | 4 | 5 | 4 | 5 | 4 |
| Formulation Example 3 | 4 | 4 | 4 | 5 | 5 | 5 |
| Formulation Example 4 | 5 | 5 | 4 | 5 | 4 | 4 |
| Comparative Formulation Example 1 | 4 | 3 | 2 | 4 | 2 | 3 |
| Comparative Formulation Example 2 | 3 | 2 | 3 | 4 | 3 | 3 |

As seen from Table 6, Comparative Formulation Examples 1-2 showed unsatisfactory results in spreadability, softness, prevention of dryness and particle aggregation, with average scores of about 2.5. In contrast, Formulation Examples 1-4 according to the present disclosure showed very good results in all aspects, with average scores of about 4.5.

[Test Example 3] Measurement of Friction

The friction of face powders of Formulation Examples 3-4 according to the present disclosure and Comparative Formulation Example 2 when applied on skin was measured using the SUN rheometer CR500DS. The powder of the same quantity was spread on a puff and friction was evaluated while applying the powder on an artificial skin at a uniform speed of 540 mm/min. The result is given in Table 7.

TABLE 7

Face powder friction test result (unit: N)

| | Initial friction | applying region of 1 cm | applying region of 3 cm | applying region of 5 cm |
|---|---|---|---|---|
| Formulation Example 3 | 24.35 | 23.22 | 17.56 | 15.01 |
| Formulation Example 4 | 25.01 | 24.02 | 18.75 | 16.24 |
| Comparative Formulation Example 2 | 36.24 | 30.37 | 20.57 | 18.01 |

As seen from Table 7, Formulation Examples 3-4 according to the present disclosure showed significantly decreased friction in all application regions up to 5 cm when compared to Comparative Formulation Example 2. Accordingly, it can be seen that the cosmetic composition containing the organic-inorganic hybrid powder according to the present disclosure exhibits very superior applicability and soft usability.

The invention claimed is:

1. An organic-inorganic hybrid powder comprising an inorganic powder coated with a biocompatible polymer,
    wherein the biocompatible polymer is 2-methacryloyloxyethylphosphorylcholine,
    wherein the inorganic powder is titanium dioxide having a hydroxy functional group, and
    wherein a coupling agent selected from the group consisting of 3-(trimethoxysilyl)propyl methacrylate and 3-(trimethoxysilyl)propylacrylate is bonded to a surface of the inorganic powder.

2. The organic-inorganic hybrid powder according to claim 1, wherein the biocompatible polymer is comprised in an amount of 0.1-8 wt % based on the total weight of the inorganic powder.

3. A method for preparing the organic-inorganic hybrid powder according to claim 1, comprising:
    1) reacting the surface of an inorganic powder having a hydroxy functional group with a coupling agent selected from the group consisting of 3-(trimethoxysilyl)propyl methacrylate and 3-(trimethoxysilyl)propylacrylate;
    2) preparing an organic-inorganic hybrid powder by coating the inorganic powder of 1) with a biocompatible polymer; and
    3) filtering and pulverizing the organic-inorganic hybrid powder of 2).

4. The method according to claim 3, wherein 2) comprises coating the biocompatible polymer on the surface of the inorganic powder by grafting.

5. The method according to claim 3, wherein, in 1), the coupling agent is used in an amount of 0.1-10 wt % based on the weight of the inorganic powder.

6. The method according to claim 3, wherein 2) comprises coating the inorganic powder with the biocompatible polymer at 65-75° C. for 6-12 hours.

7. A cosmetic composition comprising the organic-inorganic hybrid powder according to claim 1.

8. The cosmetic composition according to claim 7, wherein the composition has improved dispersibility when applied on skin.

9. The cosmetic composition according to claim 7, wherein the composition has improved adhesion to skin.

10. The cosmetic composition according to claim 7, wherein the composition is in a form selected from a group consisting of sunblock lotion, sunblock cream, makeup base, liquid foundation, powder foundation, powder pact, face powder and compact powder.

* * * * *